United States Patent [19]

Sperinck et al.

[11] Patent Number: 4,638,675
[45] Date of Patent: Jan. 27, 1987

[54] LIQUID SAMPLING SYSTEM

[75] Inventors: William A. Sperinck, Warrington; Michael J. Hall-Wilton, Capenhurst, both of England

[73] Assignee: British Nuclear Fuels plc, Warrington, England

[21] Appl. No.: 704,597

[22] Filed: Feb. 25, 1985

[30] Foreign Application Priority Data

Mar. 9, 1984 [GB] United Kingdom ............... 8406209

[51] Int. Cl.⁴ .............................................. G01N 1/14
[52] U.S. Cl. ................................ 73/864.34; 73/864.73
[58] Field of Search ........... 73/864.35, 864.34, 864.73, 73/864.74, 863.83, 863.84

[56] References Cited

U.S. PATENT DOCUMENTS

| 2,995,037 | 8/1961 | Parker et al. | 73/864.35 |
| 4,046,011 | 9/1977 | Olsen | 73/864.35 |
| 4,450,730 | 5/1984 | Levos et al. | 73/864.35 X |
| 4,512,203 | 4/1985 | Calome-Lonjean | 73/864.34 X |

FOREIGN PATENT DOCUMENTS

| 2453473 | 5/1976 | Fed. Rep. of Germany | 73/863.83 |
| 2347671 | 11/1977 | Fed. Rep. of Germany | 73/864.35 |
| 2824153 | 12/1979 | Fed. Rep. of Germany | 73/864.35 |
| 1247657 | 10/1960 | France | 73/864.35 |
| 1360346 | 7/1974 | United Kingdom | 73/863.83 |

Primary Examiner—Stewart J. Levy
Assistant Examiner—Tom Noland
Attorney, Agent, or Firm—William R. Hinds

[57] ABSTRACT

In a sampling system, delivery and return flow pipes extend between a bulk supply and a sampling station. A needle communicates with the flow path at the sampling station and apparatus is provided for maintaining a depression at the sampling station. Pulsed pressure fluid applied to the delivery pipe propels slugs of a liquid to the sampling station. With a closed bottle located on the needle, the bottle is evacuated by the depression at the sampling station to allow sample to collect in the bottle.

5 Claims, 2 Drawing Figures

LIQUID SAMPLING SYSTEM

The present invention concerns a sampling system.

In sampling hazardous and toxic liquids, such as liquids encountered in nuclear fuel reprocessing operations, it is necessary to prevent escape or loss during sampling operations.

FEATURES AND ASPECTS OF THE INVENTION

According to the present invention a sampling system for obtaining representative samples from a bulk liquid comprises a first pipe arranged to be immersed at its lower end in the liquid and communicating at its upper end with a needle sampling station and a return flow pipe, means for maintaining a depression within the pipes and at the sampling station, a pulsed pressure fluid means communicating with the first pipe for lifting slugs of liquid to the sampling station, a needle at the sampling station and a bottle for receiving sample cooperable with the needle such that with the bottle located on the needle the bottle is evacuated by the depression at the sampling station to allow liquid to collect in the bottle and on removal of the bottle the depression ensures that liquid cannot escape at the needle.

DESCRIPTION OF THE DRAWINGS

The invention will be described further by way of example with reference to the accompanying drawings; in which.

DESCRIPTION OF THE PREFERRED EMBODIMENT

Figure 1:
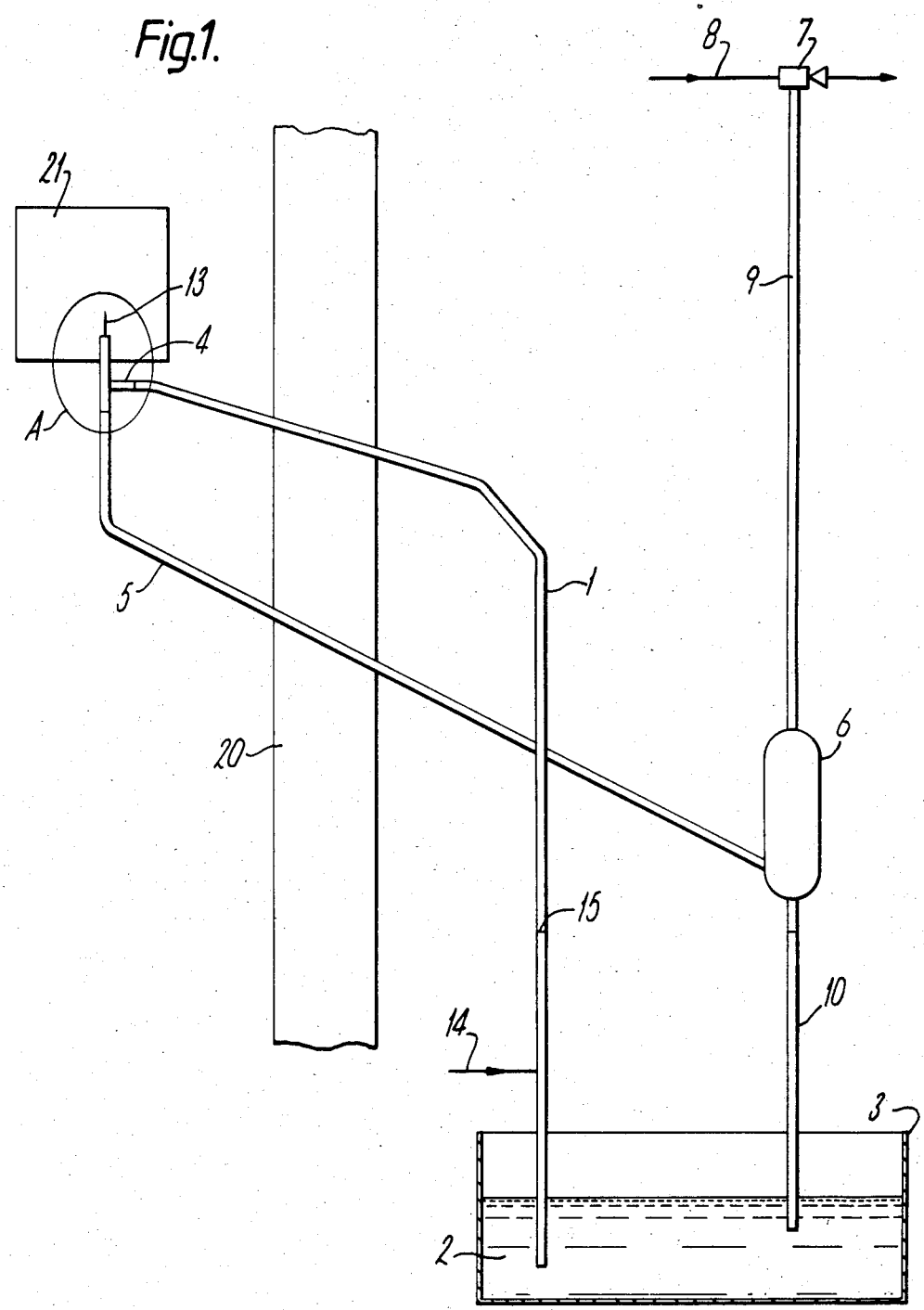
FIG. 1 is a schematic arrangement of a system for lifting liquid from a container to a sampling needle.
Figure 2:
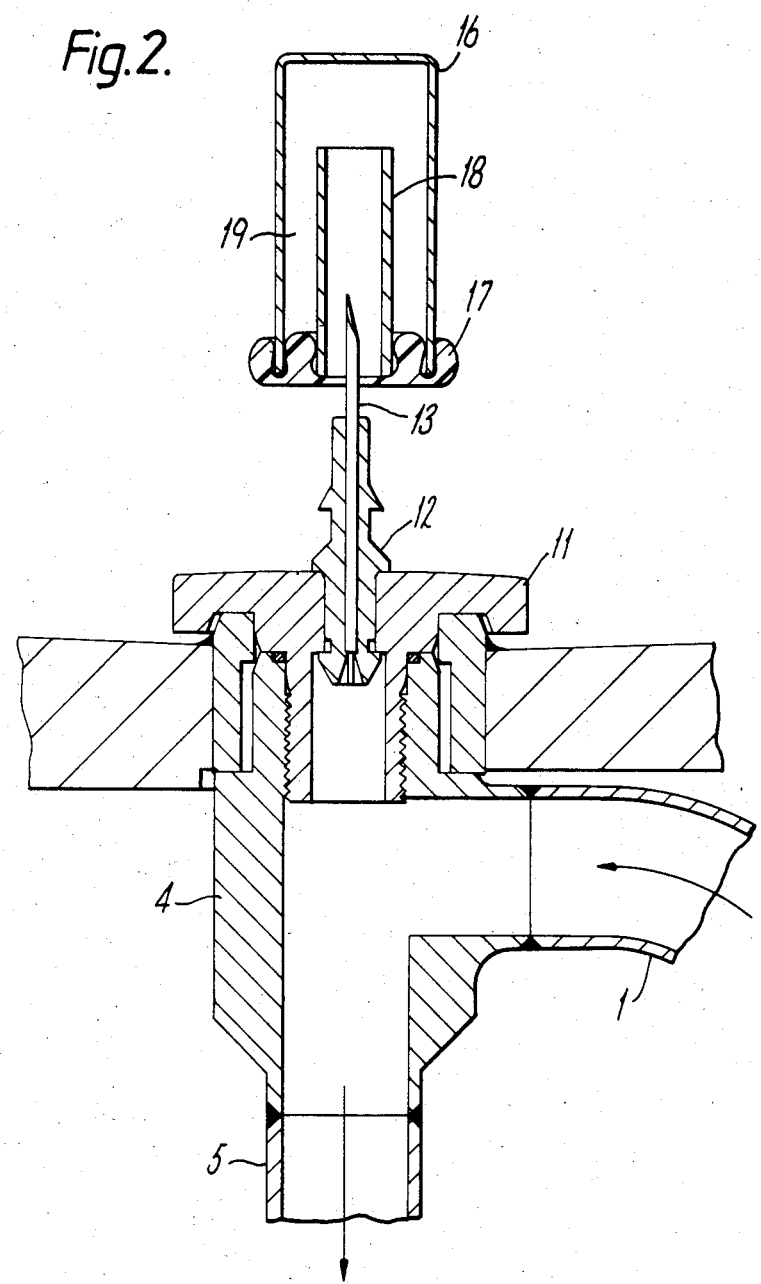
FIG. 2 is an enlarged view of the part of FIG. 1 within the region A and additionally showing a sample bottle in position.

A lower end of a pipe 1 is immersed in a liquid 2 in a tank 3. The upper end of the pipe 1 is connected to the leg of T-piece 4. One arm of the T-piece is connected to a pipe 5 which communicates with a chamber 6. An ejector 7 in a compressed gas line 8, conveniently a compressed air line, is connected by pipe 9 to the upper end of the chamber 6. A return flow pipe 10 at the lower end of the chamber 6 is immersed in the liquid 2 in the tank 3. The other arm of the T-piece 4 is closed by a plug 11 which supports a carrier 12 for a needle 13. A pressurised fluid line, conveniently a compressed air line 14, open into the pipe 1 at a position near its lower end.

In operation a supply of compressed air in line 8 and across the ejector 7 creates a depression within the chamber 6 and the pipes 1 and 5. As a result liquid from the tank 3 is drawn up the pipes 1 and 5 to a height determined by the depression and which for example can be that indicated by 15 in FIG. 1. Thereafter, compressed air in line 14 is pulsed to the liquid in the pipe 1 to lift the liquid to the T-piece 4. The liquid is delivered in discrete slugs or bursts and on reaching the T-piece 4 falls back along pipe 5 to the chamber 6. The depression created by the air ejector 7 causes air to be sucked in at the needle 13 such that liquid cannot escape through the needle while air is being sucked in.

A sample bottle 16 is provided with a rubber or the like cap 17. The bottle is placed on the needle by puncturing the cap with the needle. With the bottle in place the atmosphere within the bottle 16 is evacuated by the system depression and as a result air ceases to be sucked in at the needle 13, and sample liquid can enter and collect in the bottle. The sample enters in spurts corresponding to the slugs of liquid delivered by the compressed air admitted at line 14.

The quantity of liquid which can be collected in the bottle will depend on the length of the needle within the bottle. The level of the liquid in the bottle immediately around the needle cannot rise above the end of the needle due to the depression in the system. Various modifications can be employed to increase the quantity of liquid collected in the bottle. For example a tube 18 can be located about the needle 13 to extend above the tip of the needle. The incoming liquid spurting through the needle strikes the closed end of the bottle and falls into the annular zone 19 about the needle. The quantity of liquid which can be collected will be determined by the height of the end of the tube 18 above the tip of the needle 13.

Upon removal of the bottle containing sample from the needle the tip of the needle is immediately exposed to the atmosphere at the sampling station. As a result of the depression existing within the system any liquid or moisture at the tip is immediately sucked back into the needle and hence the T-piece 4. No liquid drop or leakage occurs at the needle tip in the absence of a bottle.

The arrangement is particularly useful for obtaining samples of radioactive liquors. The tank 3 can be located behind shielding 20 with the needle disposed outside the shielding at a sampling station 21 to receive bottles.

We claim:

1. A sampling system for obtaining representative samples from a bulk liquid comprising a first pipe arranged to be immersed at its lower end in the liquid, a needle sampling station at the opposite end of the pipe, a return flow pipe from the sampling station, means for maintaining a depression in the pipes and at the sampling station, a pulsed pressure fluid means communicating with the first pipe for lifting slugs of liquid to the sampling station, a needle at the sampling station and a bottle for receiving sample cooperable with the needle such that with the bottle located on the needle the bottle is evacuated by the depression at the sampling station to allow liquid to collect in the bottle and on removal of the bottle the depression prevents escape of liquid at the needle.

2. A sampling system according to claim 1 in which the means for maintaining the depression comprises an ejector in a compressed gas line and in communication with the return flow pipe.

3. A sampling system according to claim 1 comprising a T-piece connection at the sampling station, the leg of the T-piece being connected to the first pipe, one arm of the T-piece being connected to the return flow pipe, a plug closing the other opposite arm of the T-piece, and a carrier for the needle supported by the plug.

4. A sampling system according to claim 1 including means within the bottle to enable the level of liquid therein to rise above the tip of the needle.

5. A sampling system according to claim 4 in which said means comprises an annular zone within the bottle extending about and above the tip of the needle.

* * * * *